United States Patent [19]

Spiegelberg

[11] 4,194,624
[45] Mar. 25, 1980

[54] LOCKABLE HOLDER FOR A MULTIPLE PLASTER PACK

[75] Inventor: Hans Spiegelberg, Taby, Sweden

[73] Assignee: Salve S.A., Geneva, Switzerland

[21] Appl. No.: 952,830

[22] Filed: Oct. 20, 1978

[30] Foreign Application Priority Data

Apr. 10, 1978 [SE] Sweden .............................. 7803977

[51] Int. Cl.² ...................... A61F 13/02; A61L 15/06
[52] U.S. Cl. ..................................... 206/441; 206/1.5; 206/233
[58] Field of Search ................ 206/1.5, 214, 215, 227, 206/229, 233, 425, 495, 556, 441

[56] References Cited

U.S. PATENT DOCUMENTS

| | | | |
|---|---|---|---|
| 1,641,263 | 9/1927 | Friedman | 206/233 |
| 1,953,037 | 3/1934 | Ash | 206/1.5 |
| 3,472,362 | 10/1969 | Shimoda | 206/1.5 |
| 3,899,077 | 8/1975 | Spieglberg | 206/441 |
| 4,016,973 | 4/1977 | Blake | 206/1.5 |

FOREIGN PATENT DOCUMENTS 2278597 7/1974 Fed. Rep. of Germany ........... 206/441
2703732 1/1977 Fed. Rep. of Germany ........... 206/1.5

*Primary Examiner*—Herbert F. Ross

[57] ABSTRACT

A storage receptacle for a multiple adhesive bandage pack includes front and rear walls joined at their lower extremities and defining a trough-shaped compartment therebetween. A flange element is carried by the front wall and extends inwardly therefrom a sufficient distance to overlie at least the front wall of a multiple adhesive bandage pack which is stored within the compartment so as to prevent removal of the pack from the compartment. A plurality of apertures are formed in the front wall of the receptacle to extend therethrough below the flange element. A key member is given a set of studs corresponding in number and arrangement to the number and arrangement of the apertures in the front wall of the receptacle. The studs are insertable through the apertures to thereby engage the front wall of the pack and cause the pack to shift so that the front wall thereof moves from beneath the flange element to thereby permit removal of the pack from the storage receptacle.

16 Claims, 6 Drawing Figures

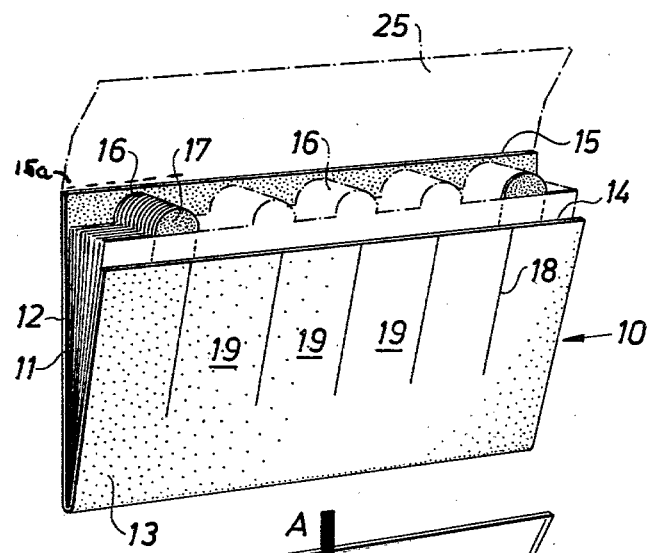
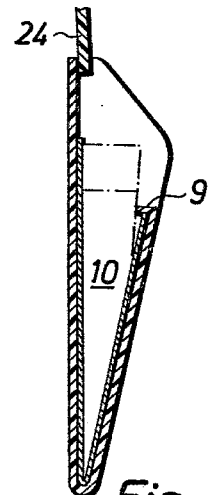
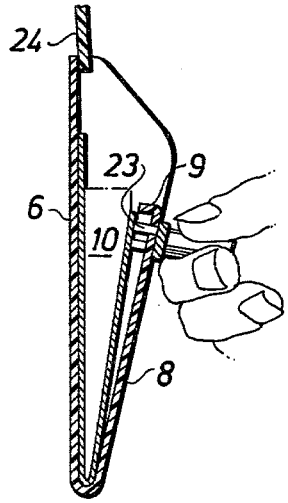
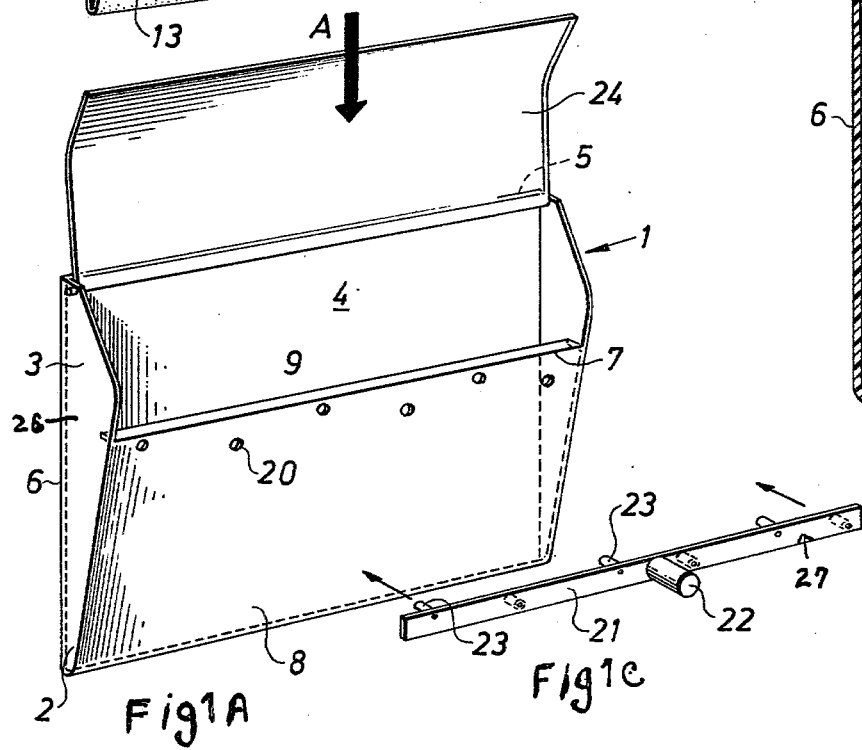

LOCKABLE HOLDER FOR A MULTIPLE PLASTER PACK

BACKGROUND OF THE INVENTION

The present invention relates to a storage receptacle for a multiple adhesive bandage pack and to the combination of the receptacle and pack.

As is known, adhesive bandages generally consist of a sterile and/or absorbent pad and adhesive zones disposed on each side of the pad for securing the bandage in place over the wound to be protected. One form of adhesive bandage utilizes tear-off protective foils over the bandage. Such bandage is positioned within an outer cover that is secured in a multiple adhesive bandage pack. Each bandage projects at one end thereof through an opening in the outer cover. The protective foil covering the sterile pad and the adhesive zone of the bandage located closest to the end of the outer cover opposite from the opening therein is arranged so as to be forcibly removed from such adhesive zone when the bandage is withdrawn from the outer cover. The adhesive zone thus exposed is prevented from coming into contact with the inner wall surface of the outer cover. A construction of this type is shown in Published Swedish Patent specification 12/12 997 or U.S. Pat. No. 3,899,077.

To facilitate the storage of a supply of adhesive bandages, resort has been had to multiple adhesive bandage packs, which packs are customarily placed for safe keeping and ready accessibility in a centrally located stationary storage receptacle. Such storage of adhesive bandage supplies have proven quite handy for offices and factories where minor wounds can thus receive prompt attention. However, the pack is not infrequently removed from the storage receptacle and, subsequent to treatment of the wound, the pack and its supply of adhesive bandages are inadvertently left at the scene of the accident which is generally remote from the location where the storage receptacle is maintained. As will be appreciated, the advantage of a centrally located storage receptacle providing a ready supply of adhesive bandages is thus negated since the next individual seeking a bandage from the storage receptacle will find the pack and its bandages missing.

SUMMARY OF THE INVENTION

It is, therefore, the principal object of this invention to provide a storage receptacle for a multiple adhesive bandage pack which will permit removal of adhesive bandages but which will prevent the unintentional removal of the pack from the receptacle.

Another object of the invention is to provide a combination of a storage receptacle for a multiple adhesive bandage pack and such a pack wherein the receptacle and the pack are cooperable so as to prevent unintentional removal of the pack while nevertheless permitting the removal of as many adhesive bandages as desired.

Other objects and advantages of the invention will become readily apparent to persons skilled in the art from the ensuing description of the invention.

According to the present invention there is provided a storage receptacle for a pack containing multiple adhesive bandages and comprising: front and rear walls joined together at the lower regions thereof and defining a trough-shaped compartment therebetween; a flange element extending inwardly from said front wall a sufficient distance so as to overlie at least the front wall of an adhesive bandage-containing pack stored in said compartment so as to prevent removal of the pack from the compartment; and a plurality of apertures extending through the front wall of said compartment below said flange element whereby a key member can be inserted through said apertures for engagement with the front wall of a pack in the compartment to shift such front wall from beneath the flange element to permit removal of the pack.

According to the present invention there is also provided the combination of a pack for multiple adhesive bandages and a storage receptacle for said pack comprising: a multiple adhesive bandage pack including front and rear walls joined adjacent the lower extremities hereof and defining therebetween a plurality of laterally arranged pockets each of which pockets is dimensioned to receive therein a plurality of vertically positioned adhesive bandages in face-to-face relationship; and a storage receptacle including front and rear walls joined together at the lower regions thereof and defining a trough-shaped compartment therebetween configured and dimensioned to accomodate said pack therein, a flange element on the front wall of said receptacle extending inwardly therefrom to overlie the front wall of a pack positioned within said compartment to thereby prevent removal of the pack from the compartment, and a plurality of apertures extending through the front wall of the receptacle below said flange element, whereby when a pack is positioned within the compartment insertion of a key member through the apertures engages the front wall of the pack and urges such front wall from beneath said flange element thereby freeing the pack for removal from the compartment.

BRIEF DESCRIPTION OF THE DRAWINGS

In order that the invention may be fully comprehended it will now be described, by way of example, with reference to the accompanying drawings in which;

FIGS. 1A-C are perspective views respectively of a storage receptacle, multiple adhesive bandage pack to be positioned therein, and a key for use therewith;

FIG. 2a is an end view in cross-section showing a storage receptacle with a multiple adhesive bandage pack releaseably locked therein;

FIG. 2b is an end view similar to that of FIG. 2a except that it depicts the pack shifted by the key such that it can be removed from the receptacle.

DESCRIPTION OF THE PREFERRED EMBODIMENTS

Figure 3:
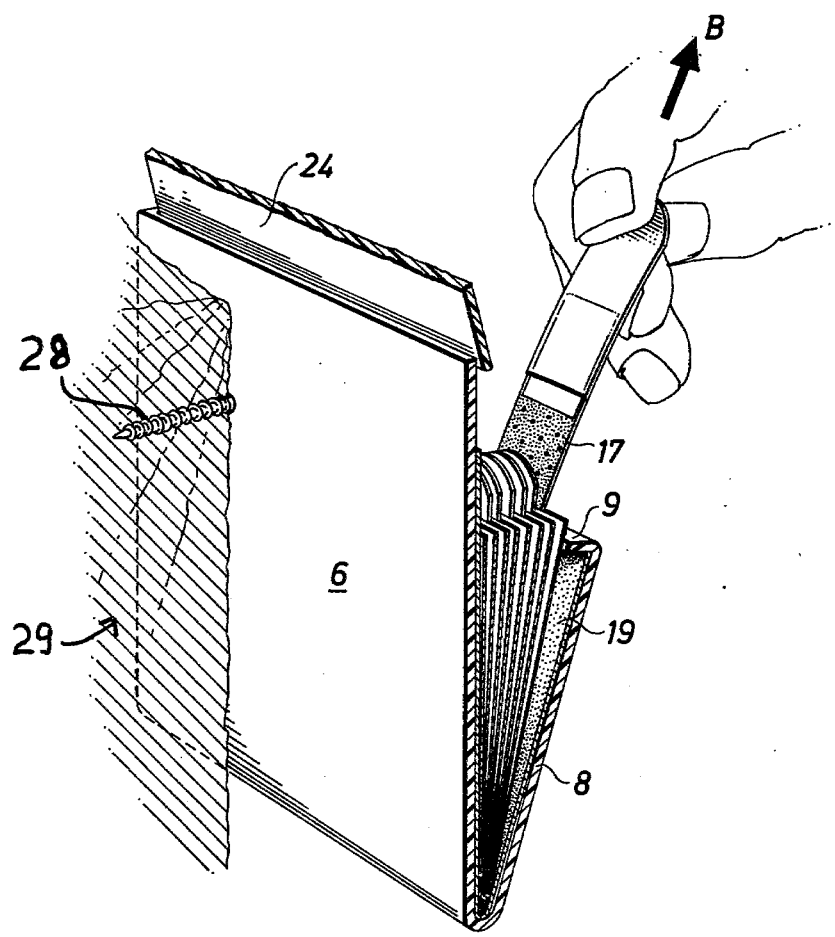
FIG. 3 is a perspective view of a storage receptacle as shown in FIG. 1 with the pack therein illustrating the removal of an adhesive bandage while the pack is restrained against unintentional removal.

Referring to the drawings there is shown a storage receptacle 1 for a multiple adhesive bandage pack 10. The receptacle includes a rear wall 6 and a front wall 8 both of which walls are substantially flat and are joined together at their lower regions so as to define a trough-shaped compartment 4 therebetween. Preferably the front and rear walls are inclined relative to each other such that compartment 4 tapers upwardly and outwardly. As can be seen from FIG. 1 and end wall 26 extends between the front and rear walls of the receptacle at each of the lateral extremities of such walls. The lower portion of the end wall 26 is relatively narrow as shown by reference numeral 2 whereas the upper portion of the end wall is wider as shown by reference numeral 3.

The front wall is is formed with a flange element 9 which extends inwardly therefrom a sufficient distance such that when the pack 10 is positioned within the compartment 4 of the storage receptacle the flange will overlie a portion of the pack, desirably the front wall thereof, so as to prevent the unintentional removal of the pack from the compartment. In the preferred form of the invention front wall 8 terminates in an upper edge 7, such upper edge being located at a lower level than upper edge 5 of the rear wall of the receptacle. Flange element 9 is desirably integral with and extends inwardly from upper edge 7 of the front wall.

Referring further to FIG. 1 there is shown a multiple adhesive bandage pack 10 in the form of a plurality of bandages, in paper or foil wrappers of the type shown in the aforementioned Swedish and U.S. Patents located between a substantially V-shaped jacket 11 formed of a rear wall portion 12 and a front wall portion 13. As with the receptacle, upper edge 14 of the front wall portion of the bandage pack is desirably disposed at a lower elevation than upper edge 15 of the rear wall portion.

The bandages are arranged in edge to edge sheets, with the sheets uniformly scored with vertical slits or cuts separating adjacent bandages. Several such sheets are placed and aligned back to back so that a plurality of lateral sections 19 each containing a plurality of bandages is provided as seen in FIGS. 1 and 3. The front face 13 of the pack 10 is also scored or slit along lines 18, aligned with the section score lines in the bandage sheets, so that packs complete with bandages can be formed of any selected length i.e.: sections.

The bandages themselves are supplied with paper or foil wrappers, such as that shown in the aforementioned patent, whereby on extraction from the pack, at least one end of adhesive will be automatically freed of the foil or paper covering for immediate application to the wound.

The front end rear walls of the pack 10 are inclined relative to each other in much the same fashion as the front and rear walls of the storage receptacle 1. This facilitates positioning of the pack within the receptacle such that it will be snugly received therein. The front wall 13 of the multiple adhesive bandage pack is movable relative to its rear wall and desirably the front and rear walls of the pack are yieldably biased away from each other such that the front wall is urged towards the front wall of the receptacle and into underlying relationship to flange element 9 so as to releasably lock the pack within the receptacle.

The pack 10 desirably includes a lid element 25 which constitutes an extension of the rear wall 12 of the pack. The rear wall may be scored as at 15a to provide a weakening along the upper edge 15 so that the lid element may be detached from the pack by tearing along the weakened zone before the pack is inserted in receptacle 1. As will be appreciated, the provision of such a detachable lid for the pack enables the marketing of the pack and adhesive bandages therein as a sealed unitary assembly so that it may be conveniently shipped or stored prior to its positioning within the receptacle without risk of destroying the sterility of the adhesive bandages.

The front wall of the storage receptacle 1 is provided with a series of apertures 20, which are arranged in a predetermined pattern with a lateral spacing so as to be between the slots 18 forming each of the sections 19 of the multiple adhesive bandage pack 10. The apertures 20 extend completely through front wall 8 of the receptacle and desirably are located in close proximity to the upper edge 7.

A key member 21 is provided consisting of a common elongated strip or bar element 27 which carries a plurality of stud elements 23 and a handle element 22. The studs 23 are configured and dimensioned to be insertable with apertures 20 of the receptacle and are arranged on bar element 27 in a pattern which is assured of engaging the face of the bandages in each of the sections 19. From FIG. 2b it can be seen that by inserting the key in the openings 20 the front wall 13 can be pushed to the rear so that all the bandage sections 19 of the plaster pack are simultaneously pressed forward from under the stop flange 9 so that the pack can be lifted out of the holder 1.

In order to provide a protective covering over the pack 10 when it is positioned within the receptacle a lid 24 is provided and carried privotably by the rear wall of the receptacle. Thus, when desired the lid may be pivoted so as to cover compartment 4.

Screw means 28 or a self adhesive backing may be formed on the rear wall 6 for the purpose of mounting the storage receptacle upon a wall 29. Although the storage receptacle may be constructed of any suitable rigid material such as wood, metal and the like, the use of an attractively colored plastic material is presently preferred. The multiple adhesive bandage pack 10 may be constructed from cardboard or any other suitable material; however, relative movement between the front and rear wall of the pack is important, and if need be the front and rear wall may be connected at their lower extremities by a separate or a self hinge to provide the desired relative movement and resiliency.

Cooperation between the pack and storage receptacle will now be described. As shown in FIG. 1, when the pack is lowered into position within the receptacle by movement in the direction of arrow A the front wall of the pack moves downwardly past flange element 9 until the upper edge of the front wall of the pack moves past the flange element. At such time the front wall shifts forardly so as to lie beneath the flange element. This is shown in FIG. 2a where pack 10 is releasably locked within the storage receptacle. As shown in FIG. 3. Although the pack is locked within the receptacle one may have access to the adhesive bandages within the pack from whence they may be withdrawn in the direction of arrow B. It will be observed from FIG. 3 that when the upper end of one of the adhesive bandages is pulled into the direction of arrow B one of the adhesive zones of the bandage, i.e. the lower adhesive zone is forcibly exposed so that the bandage can be applied to the skin with the exposed adhesive zone, the other protective foil then removed and the other adhesive zone of the bandage adhered to the skin. However, the pack remains locked within the storage receptacle. In the event that for some reason it is considered desirable to remove the pack from the receptacle key 21 is manipulated such that the studs 23 thereof are inserted into apertures 20 of the front wall 8 of receptacle 1. As shown in FIG. 2b, upon insertion of the studs 23 into apertures 20 engagement with the front wall of the pack will take place so that such front wall is shifted from beneath flange element 9. Such shifting of the front wall 13 of the multiple adhesive bandage pack frees same from the flange element and permits the removal of the pack from compartment 4 of the storage receptacle.

It will be understood, of course, that apertures 20 may have any configuration desired and that the number of such apertures and the pattern thereof may be varied as desired. Further, although flange element 9 is shown as being integral with the upper edge of the front wall of the receptacle the flange may be located below the upper edge. It will, of course, be recognized that the construction of the multiple adhesive bandage pack would have to modified in order to provide the required cooperation between the front wall of the pack and the front wall and flange element of the receptacle. It is also within the contemplation of this invention to eliminate the rear wall of the pack 10 and to make provisions for positioning of the adhesive bandages such that they are still secured properly within the pack.

It will be appreciated, from the foregoing description of the invention, that a storage receptacle has been provided which obviate the problem discussed above and that when employed with the multiple adhesive bandage pack disclosed herein the advantages of a centrally located storage receptacle providing a ready supply of adhesive bandages will be assured.

I claim:

1. A storage receptable for a separable pack having at least a front wall behind which multiple adhesive bandages are located comprising: front and rear walls joined together at the lower regions thereof and defining a trough-shaped compartment therebetween; a flange element extending inwardly from said front wall a sufficient distance so as to overlie at least the front wall of the adhesive bandage-containing pack stored in said compartment so as to prevent removal of the pack from the compartment but permit removal of individual bandages; and a plurality of apertures extending through the front wall of said compartment below said flange element whereby a key member can be inserted through said apertures for engagement with the front wall of a pack in the compartment to shift such front wall from beneath the flange element to permit removal of the pack.

2. A storage receptacle according to claim 1, wherein said front and rear walls thereof are inclined relative to each other so as to provide a compartment which tapers upwardly and outwardly.

3. A storage receptacle according to claim 1 or 2, wherein said front wall thereof terminates in an upper edge which is at a lower level than an upper edge of the rear wall of the receptacle, said flange element being integral with and extending inwardly from the upper edge of said front wall.

4. A storage receptacle according to claim 3, wherein said apertures are arranged in laterally spaced symmetrical pattern proximate said upper edge of said front wall.

5. A storage receptacle according to claim 4, wherein the lateral spacing between said apertures is selected to correspond with adjacently arranged sections of a multiple adhesive bandage pack.

6. A storage receptacle according to claim 1, including a lid member carried pivotably by the rear wall thereof for selectively covering said trough-shaped compartment.

7. A storage receptacle according to claim 1, including a key member having a plurality of studs projecting therefrom insertable through respective ones of said apertures.

8. A storage receptacle according to claim 1, including end walls extending between the outer lateral extremities of the front and rear walls of the receptacle.

9. The combination of a pack having at least front wall behind which multiple adhesive bandages are located and a storage receptacle for said pack comprising: a multiple adhesive bandage pack including front and rear walls joined adjacent the lower extremities hereof and defining therebetween a plurality of laterally arranged sections each of which sections is dimensioned to receive therein a plurality of vertically positioned adhesive bandages in face-to-face relationship; and a storage receptacle including front and rear walls joined together at the lower regions therebetween configured and dimensioned to accomodate said pack therein, a flange element on the front wall of said receptacle extending inwardly therefrom to overlie the front wall of a pack postioned within said compartment to thereby prevent removal of the pack from the compartment while permitting removal of the individual bandages, and a plurality of apertures extending through the front wall of the receptacle below said flange element, whereby when a pack is positioned within the compartment insertion of a key member through the apertures engages the front wall of the pack and urges such front wall from beneath said flange thereby freeing the pack for removal from the compartment.

10. The combination of claim 9, wherein the front and rear walls of the receptacle and the front and rear walls of the pack are respectively inclined relative to each other.

11. The combination of claim 9 or 10, wherein the front and rear walls of said pack are movable relative to each other.

12. The combination of claim 11, wherein said front and rear walls of the pack are yieldably biased away from each other.

13. The combination of claim 9, including a key member having a pluraliby of studs projecting therefrom insertable through respective ones of said apertures so as to be engageable with the front wall of the pack.

14. The combination of claim 9, including a lid member carried pivotably by the rear wall of the receptacle for selectively covering the compartment thereof.

15. The combination of claim 9, including end walls extending between the outer lateral extremities of the front and rear walls of said storage receptacle.

16. The combination of claim 9, including a lid element constituting an extension of the rear wall of said pack, said rear wall having at least one weakened zone formed thereon at a predetermined location to permit detachment of said lid element by tearing along said weakened zone.

* * * * *